(12) United States Patent
Romo (10) Patent No.: US 10,149,720 B2
(45) Date of Patent: Dec. 11, 2018

(54) METHOD, APPARATUS, AND A SYSTEM FOR FACILITATING BENDING OF AN INSTRUMENT IN A SURGICAL OR MEDICAL ROBOTIC ENVIRONMENT

(71) Applicant: Auris Health, Inc., Redwood City, CA (US)

(72) Inventor: Enrique Romo, Dublin, CA (US)

(73) Assignee: Auris Health, Inc., Redwood City, CA (US)

( * ) Notice: Subject to any disclaimer, the term of this patent is extended or adjusted under 35 U.S.C. 154(b) by 473 days.

(21) Appl. No.: 14/201,610

(22) Filed: Mar. 7, 2014

(65) Prior Publication Data

US 2015/0101442 A1    Apr. 16, 2015

Related U.S. Application Data

(60) Provisional application No. 61/774,901, filed on Mar. 8, 2013.

(51) Int. Cl.
| | |
|---|---|
| *A61B 1/008* | (2006.01) |
| *A61B 19/00* | (2006.01) |
| *A61B 1/005* | (2006.01) |
| *A61B 17/00* | (2006.01) |
| *A61B 34/30* | (2016.01) |
| *A61M 25/01* | (2006.01) |

(52) U.S. Cl.
CPC ........ *A61B 19/2203* (2013.01); *A61B 1/0055* (2013.01); *A61B 1/0056* (2013.01); *A61B 17/00234* (2013.01); *A61B 34/30* (2016.02); *A61M 25/0138* (2013.01); *A61B 2034/301* (2016.02); *A61B 2034/306* (2016.02); *Y10T 74/20323* (2015.01)

(58) Field of Classification Search
CPC ............ A61B 1/0055; A61B 17/00234; A61B 19/2203; A61B 1/0057; B25J 9/065; B25J 9/104; B25J 9/1054
USPC ............... 74/490.04; 600/141, 142, 146, 153
See application file for complete search history.

(56) References Cited

U.S. PATENT DOCUMENTS

| | | | |
|---|---|---|---|
| 3,572,325 | A | 3/1971 | Bazell et al. |
| 4,580,551 | A | 4/1986 | Siegmund et al. |
| 4,597,388 | A | 7/1986 | Koziol et al. |
| 4,700,693 | A | 10/1987 | Lia |
| 4,721,097 | A | 1/1988 | D'Amelio |
| 4,745,908 | A | 5/1988 | Wardle |
| 4,748,969 | A | 6/1988 | Wardle |

(Continued)

FOREIGN PATENT DOCUMENTS

| | | | |
|---|---|---|---|
| CN | 1839764 | A | 10/2006 |
| CN | 102088920 | A | 6/2011 |

(Continued)

OTHER PUBLICATIONS

U.S. Appl. No. 14/542,373, filed Nov. 14, 2014, Romo et al.

(Continued)

*Primary Examiner* — William C Joyce
(74) *Attorney, Agent, or Firm* — Knobbe, Martens, Olson & Bear, LLP (57) ABSTRACT

An instrument that facilitates bending with large degrees of articulation while maintaining ease of manufacturing for medical and surgical applications is discussed.

18 Claims, 7 Drawing Sheets

(56) References Cited

U.S. PATENT DOCUMENTS

| | | | |
|---|---|---|---|
| 4,869,238 A * | 9/1989 | Opie | A61B 1/00071 600/109 |
| 4,905,673 A | 3/1990 | Pimiskern | |
| 4,907,168 A | 3/1990 | Boggs | |
| 4,911,148 A | 3/1990 | Sosnowski et al. | |
| 5,106,387 A | 4/1992 | Kittrell et al. | |
| 5,168,864 A | 12/1992 | Shockey | |
| 5,287,861 A | 2/1994 | Wilk | |
| 5,313,934 A | 5/1994 | Wiita et al. | |
| 5,381,782 A | 1/1995 | Delarama et al. | |
| 5,425,735 A | 6/1995 | Rosen et al. | |
| 5,462,561 A | 10/1995 | Vada | |
| 5,472,406 A | 12/1995 | De La Torre et al. | |
| 5,477,856 A | 12/1995 | Lundquist | |
| 5,507,725 A | 4/1996 | Savage et al. | |
| 5,572,999 A | 11/1996 | Funda et al. | |
| 5,662,590 A | 9/1997 | De La Torre et al. | |
| 5,695,500 A | 12/1997 | Taylor et al. | |
| 5,704,534 A * | 1/1998 | Huitema | A61B 17/07207 227/175.1 |
| 5,873,817 A * | 2/1999 | Kokish | A61B 1/0058 600/143 |
| 5,876,325 A | 3/1999 | Mizuno et al. | |
| 5,910,129 A * | 6/1999 | Koblish | A61B 18/1492 604/159 |
| 5,928,163 A | 7/1999 | Roberts et al. | |
| 6,012,494 A * | 1/2000 | Balazs | B25J 18/06 138/110 |
| 6,019,772 A | 2/2000 | Shefaram et al. | |
| 6,033,371 A | 3/2000 | Torre et al. | |
| 6,157,853 A | 12/2000 | Blume et al. | |
| 6,198,974 B1 | 3/2001 | Webster, Jr. | |
| 6,326,616 B1 | 12/2001 | Andrien et al. | |
| 6,398,792 B1 | 6/2002 | O'Connor | |
| 6,406,486 B1 | 6/2002 | De La Torre et al. | |
| 6,436,107 B1 | 8/2002 | Wang et al. | |
| 6,491,626 B1 * | 12/2002 | Stone | A61B 1/00 403/291 |
| 6,554,793 B1 | 4/2003 | Pauker et al. | |
| 6,638,246 B1 | 10/2003 | Naimark et al. | |
| 6,671,581 B2 | 12/2003 | Niemeyer et al. | |
| 6,716,178 B1 | 4/2004 | Kilpatrick et al. | |
| 6,736,784 B1 | 5/2004 | Menne et al. | |
| 6,763,259 B1 | 7/2004 | Hauger et al. | |
| 6,827,712 B2 | 12/2004 | Tovey et al. | |
| 6,932,824 B1 | 8/2005 | Roop | |
| 7,008,401 B2 | 3/2006 | Thompson et al. | |
| 7,087,061 B2 | 8/2006 | Chernenko et al. | |
| 7,130,700 B2 * | 10/2006 | Gardeski | A61M 25/0021 600/585 |
| 7,344,528 B1 | 3/2008 | Tu et al. | |
| 7,351,193 B2 | 4/2008 | Forman et al. | |
| 7,725,214 B2 | 5/2010 | Diolaiti | |
| 7,883,475 B2 | 2/2011 | Dupont et al. | |
| 7,930,065 B2 | 4/2011 | Larkin et al. | |
| 7,967,799 B2 | 6/2011 | Boukhny | |
| 8,049,873 B2 | 11/2011 | Hauger et al. | |
| 8,052,636 B2 | 11/2011 | Moll et al. | |
| 8,224,484 B2 | 7/2012 | Swarup et al. | |
| 8,256,428 B2 | 9/2012 | Hindricks et al. | |
| 8,292,827 B2 | 10/2012 | Musbach et al. | |
| 8,414,564 B2 | 4/2013 | Goldshleger et al. | |
| 8,444,637 B2 * | 5/2013 | Podmore | A61B 17/00234 604/95.04 |
| 8,498,691 B2 | 7/2013 | Moll et al. | |
| 8,515,215 B2 | 8/2013 | Younge et al. | |
| 8,518,024 B2 | 8/2013 | Williams et al. | |
| 8,602,031 B2 | 12/2013 | Reis et al. | |
| 8,720,448 B2 | 5/2014 | Reis et al. | |
| 8,821,477 B2 | 9/2014 | Northrop et al. | |
| 8,827,947 B2 | 9/2014 | Bosman et al. | |
| 8,827,948 B2 | 9/2014 | Romo et al. | |
| 8,894,610 B2 | 11/2014 | MacNamara et al. | |
| 8,961,533 B2 | 2/2015 | Stahler et al. | |
| 9,186,046 B2 | 11/2015 | Ramamurthy et al. | |
| 9,204,933 B2 | 12/2015 | Reis et al. | |
| 9,254,123 B2 | 2/2016 | Alvarez et al. | |
| 9,408,669 B2 | 8/2016 | Kokish et al. | |
| 9,427,551 B2 | 8/2016 | Leeflang et al. | |
| 9,462,932 B2 | 10/2016 | Ostrovsky et al. | |
| 9,504,604 B2 | 11/2016 | Alvarez | |
| 9,561,083 B2 | 2/2017 | Yu et al. | |
| 9,591,990 B2 | 3/2017 | Chen et al. | |
| 9,622,827 B2 | 4/2017 | Yu et al. | |
| 9,636,184 B2 | 5/2017 | Lee et al. | |
| 9,713,509 B2 | 7/2017 | Schuh et al. | |
| 9,727,963 B2 | 8/2017 | Mintz et al. | |
| 9,737,371 B2 | 8/2017 | Romo et al. | |
| 9,737,373 B2 | 8/2017 | Schuh | |
| 9,744,335 B2 | 8/2017 | Jiang | |
| 9,788,910 B2 | 10/2017 | Schuh | |
| 10,016,900 B1 | 7/2018 | Meyer et al. | |
| 10,022,192 B1 | 7/2018 | Ummalaneni | |
| 2003/0195664 A1 | 10/2003 | Nowlin et al. | |
| 2004/0015122 A1 | 1/2004 | Zhang et al. | |
| 2004/0030349 A1 | 2/2004 | Boukhny | |
| 2004/0059257 A1 | 3/2004 | Gaber | |
| 2004/0135733 A1 | 7/2004 | Chou et al. | |
| 2004/0138525 A1 * | 7/2004 | Saadat | A61B 1/0055 600/104 |
| 2004/0138529 A1 | 7/2004 | Wiltshire | |
| 2005/0004515 A1 | 1/2005 | Hart et al. | |
| 2005/0070844 A1 | 3/2005 | Chow et al. | |
| 2005/0125005 A1 | 6/2005 | Fujikura | |
| 2005/0154262 A1 | 7/2005 | Banik et al. | |
| 2005/0159646 A1 | 7/2005 | Nordstrom et al. | |
| 2005/0197623 A1 | 9/2005 | Leeflang | |
| 2005/0272975 A1 | 12/2005 | McWeeney et al. | |
| 2006/0041188 A1 * | 2/2006 | Dirusso | A61B 1/0055 600/146 |
| 2006/0111692 A1 | 5/2006 | Hlavka et al. | |
| 2006/0173243 A1 | 8/2006 | Watanabe | |
| 2006/0276827 A1 | 12/2006 | Mitelberg et al. | |
| 2007/0032906 A1 | 2/2007 | Sutherland et al. | |
| 2007/0060879 A1 | 3/2007 | Weitzner et al. | |
| 2007/0135733 A1 | 6/2007 | Soukijp et al. | |
| 2007/0135763 A1 | 6/2007 | Musbach et al. | |
| 2007/0135803 A1 | 6/2007 | Belson | |
| 2007/0270645 A1 | 11/2007 | Ikeda | |
| 2007/0270679 A1 | 11/2007 | Nguyen et al. | |
| 2007/0282167 A1 | 12/2007 | Barenboym et al. | |
| 2007/0287886 A1 | 12/2007 | Saadat | |
| 2007/0299427 A1 | 12/2007 | Yeung et al. | |
| 2008/0051629 A1 | 2/2008 | Sugiyama et al. | |
| 2008/0064921 A1 | 3/2008 | Larkin | |
| 2008/0065103 A1 | 3/2008 | Cooper et al. | |
| 2008/0065109 A1 | 3/2008 | Larkin | |
| 2008/0097293 A1 | 4/2008 | Chin et al. | |
| 2008/0108869 A1 | 5/2008 | Sanders et al. | |
| 2008/0114341 A1 | 5/2008 | Thyzel | |
| 2008/0177285 A1 | 7/2008 | Brock et al. | |
| 2008/0187101 A1 | 8/2008 | Gertner | |
| 2008/0208001 A1 * | 8/2008 | Hadani | A61B 1/0055 600/128 |
| 2008/0212082 A1 | 9/2008 | Froggatt et al. | |
| 2008/0218770 A1 | 9/2008 | Moll et al. | |
| 2008/0228104 A1 | 9/2008 | Uber et al. | |
| 2008/0249483 A1 | 10/2008 | Sienker | |
| 2009/0099420 A1 | 4/2009 | Woodley et al. | |
| 2009/0137952 A1 | 5/2009 | Ramamurthy et al. | |
| 2009/0171271 A1 | 7/2009 | Webster et al. | |
| 2009/0247880 A1 | 10/2009 | Naruse et al. | |
| 2009/0248041 A1 | 10/2009 | Williams et al. | |
| 2009/0248043 A1 | 10/2009 | Tierney et al. | |
| 2009/0254083 A1 | 10/2009 | Wallace et al. | |
| 2009/0262109 A1 | 10/2009 | Markowitz et al. | |
| 2009/0264878 A1 | 10/2009 | Carmel et al. | |
| 2009/0268015 A1 | 10/2009 | Scott et al. | |
| 2009/0312768 A1 | 12/2009 | Hawkins et al. | |
| 2009/0326322 A1 | 12/2009 | Diolaiti | |
| 2010/0030023 A1 | 2/2010 | Yoshie | |
| 2010/0036294 A1 | 2/2010 | Mantell et al. | |
| 2010/0073150 A1 | 3/2010 | Olson et al. | |

(56) References Cited

U.S. PATENT DOCUMENTS

| | | | |
|---|---|---|---|
| 2010/0114115 A1 | 5/2010 | Schlesinger et al. | |
| 2010/0130823 A1* | 5/2010 | Ando | A61B 1/00071 |
| | | | 600/141 |
| 2010/0228191 A1 | 9/2010 | Alvarez et al. | |
| 2010/0331856 A1 | 12/2010 | Carlson et al. | |
| 2011/0009779 A1 | 1/2011 | Romano et al. | |
| 2011/0152880 A1 | 1/2011 | Alvarez et al. | |
| 2011/0028887 A1 | 2/2011 | Fischer et al. | |
| 2011/0040404 A1 | 2/2011 | Diolaiti et al. | |
| 2011/0046411 A1 | 2/2011 | Ohrlein et al. | |
| 2011/0046441 A1 | 2/2011 | Wiltshire et al. | |
| 2011/0071508 A1 | 3/2011 | Duval | |
| 2011/0106102 A1 | 5/2011 | Balicki et al. | |
| 2011/0130718 A1 | 6/2011 | Kidd et al. | |
| 2011/0237888 A1 | 9/2011 | Matsushita | |
| 2011/0261183 A1 | 10/2011 | Ma et al. | |
| 2011/0306836 A1 | 12/2011 | Ohline et al. | |
| 2012/0071894 A1 | 3/2012 | Tanner et al. | |
| 2012/0123327 A1 | 5/2012 | Miller | |
| 2012/0136419 A1 | 5/2012 | Zarembo et al. | |
| 2012/0138586 A1 | 6/2012 | Webster et al. | |
| 2012/0143226 A1 | 6/2012 | Belson et al. | |
| 2012/0191107 A1 | 7/2012 | Tanner et al. | |
| 2012/0239012 A1 | 9/2012 | Laurent et al. | |
| 2012/0259244 A1* | 10/2012 | Roberts | A61M 16/0486 |
| | | | 600/586 |
| 2012/0283747 A1 | 11/2012 | Popovic | |
| 2013/0018400 A1 | 1/2013 | Milton et al. | |
| 2013/0030519 A1 | 1/2013 | Tran et al. | |
| 2013/0035537 A1 | 2/2013 | Wallace et al. | |
| 2013/0072787 A1 | 3/2013 | Wallace et al. | |
| 2013/0090552 A1 | 4/2013 | Ramamurthy et al. | |
| 2013/0144116 A1 | 6/2013 | Cooper et al. | |
| 2013/0165854 A1 | 6/2013 | Sandhu et al. | |
| 2013/0165908 A1* | 6/2013 | Purdy | A61F 5/0013 |
| | | | 606/1 |
| 2013/0317276 A1 | 11/2013 | D'Andrea | |
| 2013/0317519 A1 | 11/2013 | Romo et al. | |
| 2013/0345519 A1 | 12/2013 | Piskun et al. | |
| 2014/0012276 A1 | 1/2014 | Alvarez | |
| 2014/0046313 A1 | 2/2014 | Pederson et al. | |
| 2014/0069437 A1 | 3/2014 | Reis et al. | |
| 2014/0142591 A1 | 5/2014 | Alvarez et al. | |
| 2014/0276391 A1 | 9/2014 | Yu | |
| 2014/0276594 A1 | 9/2014 | Tanner et al. | |
| 2014/0309649 A1 | 10/2014 | Alvarez et al. | |
| 2014/0357984 A1 | 12/2014 | Wallace et al. | |
| 2014/0364870 A1 | 12/2014 | Alvarez et al. | |
| 2014/0379000 A1 | 12/2014 | Romo et al. | |
| 2015/0025539 A1 | 1/2015 | Alvarez et al. | |
| 2015/0051592 A1 | 2/2015 | Kintz | |
| 2015/0101442 A1 | 4/2015 | Romo | |
| 2015/0119637 A1 | 4/2015 | Alvarez et al. | |
| 2015/0119638 A1 | 4/2015 | Yu et al. | |
| 2015/0164594 A1 | 6/2015 | Romo et al. | |
| 2015/0164595 A1 | 6/2015 | Bogusky et al. | |
| 2015/0164596 A1 | 6/2015 | Romo et al. | |
| 2015/0335480 A1 | 11/2015 | Alvarez et al. | |
| 2016/0001038 A1 | 1/2016 | Romo et al. | |
| 2016/0007881 A1 | 1/2016 | Wong et al. | |
| 2016/0151122 A1 | 6/2016 | Alvarez et al. | |
| 2016/0270865 A1 | 9/2016 | Landey et al. | |
| 2016/0287279 A1 | 10/2016 | Bovay et al. | |
| 2016/0287346 A1 | 10/2016 | Hyodo et al. | |
| 2016/0296294 A1 | 10/2016 | Moll et al. | |
| 2016/0338783 A1 | 11/2016 | Romo et al. | |
| 2016/0338785 A1 | 11/2016 | Kokish et al. | |
| 2016/0346049 A1 | 12/2016 | Allen et al. | |
| 2016/0374541 A1 | 12/2016 | Agrawal et al. | |
| 2016/0374590 A1 | 12/2016 | Wong et al. | |
| 2017/0007337 A1 | 1/2017 | Dan | |
| 2017/0065364 A1 | 3/2017 | Schuh et al. | |
| 2017/0065365 A1 | 3/2017 | Schuh | |
| 2017/0100199 A1 | 4/2017 | Yu et al. | |
| 2017/0119411 A1 | 5/2017 | Shah | |
| 2017/0119412 A1 | 5/2017 | Noonan et al. | |
| 2017/0119413 A1 | 5/2017 | Romo | |
| 2017/0119481 A1 | 5/2017 | Romo et al. | |
| 2017/0165011 A1 | 6/2017 | Bovay et al. | |
| 2017/0172673 A1 | 6/2017 | Yu et al. | |
| 2017/0202627 A1 | 7/2017 | Sramek et al. | |
| 2017/0209073 A1 | 7/2017 | Sramek et al. | |
| 2017/0290631 A1 | 10/2017 | Lee et al. | |
| 2017/0333679 A1 | 11/2017 | Jiang | |
| 2017/0340396 A1 | 11/2017 | Romo et al. | |
| 2017/0365055 A1 | 12/2017 | Mintz et al. | |
| 2017/0367782 A1 | 12/2017 | Schuh et al. | |
| 2018/0025666 A1 | 1/2018 | Ho et al. | |
| 2018/0055583 A1 | 3/2018 | Schuh et al. | |
| 2018/0055589 A1 | 3/2018 | Joseph et al. | |
| 2018/0177383 A1 | 6/2018 | Noonan et al. | |
| 2018/0177556 A1 | 6/2018 | Noonan et al. | |
| 2018/0177561 A1 | 6/2018 | Mintz et al. | |

FOREIGN PATENT DOCUMENTS

| | | |
|---|---|---|
| EP | 0 543 539 | 5/1993 |
| EP | 0 776 739 | 6/1997 |
| EP | 1 442 720 | 8/2004 |
| EP | 0 904 796 | 11/2004 |
| JP | H09224951 A | 9/1997 |
| JP | 2010-046384 | 3/2010 |
| JP | 2011-015992 | 1/2011 |
| WO | WO 92/14411 A1 | 9/1992 |
| WO | WO 00/67640 | 11/2000 |
| WO | WO-0105849 A1 | 1/2001 |
| WO | WO 02/074178 | 9/2002 |
| WO | WO 03/096871 A2 | 11/2003 |
| WO | WO 04/039273 | 5/2004 |
| WO | WO 2004/105849 A1 | 12/2004 |
| WO | WO 05/032637 | 4/2005 |
| WO | WO 05/081202 | 9/2005 |
| WO | WO 09/097461 | 6/2007 |
| WO | WO 08/097540 | 8/2008 |
| WO | WO 09/092059 | 7/2009 |
| WO | WO-2010081187 A1 | 7/2010 |
| WO | WO 10/088187 | 8/2010 |
| WO | WO 2011/161218 A1 | 12/2011 |
| WO | WO-2014138729 A1 | 9/2014 |
| WO | WO-2016037133 A1 | 3/2016 |

OTHER PUBLICATIONS

U.S. Appl. No. 14/542,387, filed Nov. 14, 2014, Bogusky et al.
U.S. Appl. No. 14/542,403, filed Nov. 14, 2014, Yu et al.
U.S. Appl. No. 14/542,429, filed Nov. 14, 2014, Romo et al.
Office action dated Oct. 7, 2014 for U.S. Appl. No. 13/711,440.
U.S. Appl. No. 14/578,082, filed Dec. 19, 2014, Alvarez et al.
U.S. Appl. No. 14/583,021, filed Dec. 24, 2014, Romo et al.
International search report and written opinion dated Jan. 27, 2015 for PCT Application No. US2014/062284.
International search report and written opinion dated Dec. 4, 2015 for PCT Application No. PCT/US15/48688.
European search report and search opinion dated Jul. 2, 2015 for EP Application No. 12856685.8.
Office action dated May 21, 2015 for U.S. Appl. No. 13/711,440.
Office action dated Jun. 11, 2015 for U.S. Appl. No. 14/158,548.
U.S. Appl. No. 14/196,953, filed Mar. 4, 2014, Alvarez et al.
U.S. Appl. No. 14/301,871, filed Jun. 11, 2014, Alvarez et al.
U.S. Appl. No. 14/458,042, filed Aug. 12, 2014, Kintz.
U.S. Appl. No. 14/479,095, filed Sep. 5, 2014, Romo et al.
U.S. Appl. No. 14/523,760, filed Oct. 24, 2014, Alvarez et al.
U.S. Appl. No. 62/037,520, filed Aug. 14, 2014, Yu.
Balicki, et al. Single fiber optical coherence tomography microsurgical instruments for computer and robot-assisted retinal surgery. Medical Image Computing and Computer-Assisted Intervention. MICCAI 2009. Springer Berlin Heidelberg, 2009. 108-115.
Effect of microsecond pulse length and tip shape on explosive bubble formation of 2.78 iLtm Er,Cr;YSGG and 2.94 iLtm Er:YAG laser. Paper 8221-12, Proceedings of SPIE, vol. 8221 (Monday Jan. 23, 2013).

(56) References Cited

OTHER PUBLICATIONS

Ehlers, et al. Integration of a spectral domain optical coherence tomography system into a surgical microscope for intraoperative imaging. Investigative Ophthalmology and Visual Science 52.6. 2011; 3153-3159.

Hubschman. Robotic Eye Surgery: Past, Present, and Future. Journal of Computer Science and Systems Biology. 2012.

International search report and written opinion dated Mar. 29, 2013 for PCT/US2012/069540.

International search report and written opinion dated Nov. 7, 2014 for PCT Application No. US2014/041990.

International search report dated Jun. 16, 2014 for PCT/US2014/022424.

Office action dated Jun. 19, 2014 for U.S. Appl. No. 13/868,769.

Stoyanov. Surgical vision. Annals of Biomedical Engineering 40.2. 2012; 332-345. Published Oct. 20, 2011.

European search report and search opinion dated Sep. 16, 2016 for EP Application No. 14760802.0.

Office action dated Jul. 10, 2017 for U.S. Appl. No. 14/479,095.

\* cited by examiner

METHOD, APPARATUS, AND A SYSTEM FOR FACILITATING BENDING OF AN INSTRUMENT IN A SURGICAL OR MEDICAL ROBOTIC ENVIRONMENT

CROSS-REFERENCE TO RELATED APPLICATIONS

This application claims the benefit of U.S. Provisional Application No. 61/774,901, filed Mar. 8, 2013, the entire content of which is incorporated herein by reference.

BACKGROUND OF THE INVENTION

1. Field of the Invention

The field of the present application pertains to medical devices. More particularly, the field of the invention pertains to an apparatus, system, and method for performing surgery.

2. Description of the Related Art

Robotic surgery has many benefits to improve patient recovery time and allows precise control of medical and surgical application instruments. In robotics, an end effector is the device at the end of a robotic arm, designed to interact with the environment. The exact nature of this device depends on the application of the robot. For example, several examples of end effectors could include a set of forceps, a pair of scissors, a laser, a camera, a cautery tool, a needle, or any other instrument tip that would benefit from being able to be repositioned.

As previously discussed, which originates from serial robotic manipulators, the end effector means the last link (or end) of the robot. At this endpoint the tools are attached. In a wider sense, an end effector can be seen as the part of a robot that interacts with the work environment.

Many articulating devices use bending sections comprising many small moving parts for creating an assembly. Typically, the assemblies are difficult to manufacture in smaller geometries since the individual components become difficult to fabricate.

Figure 1:
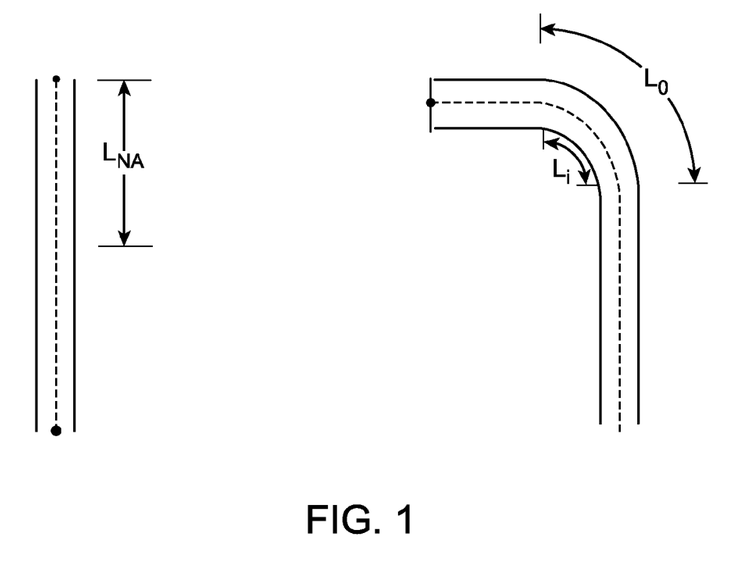
FIG. 1 is a view to facilitate description of a neutral axis.

Another challenge with existing solutions is accommodating the ancillary components for the end effector; which may include pull wire, electrical wires, fluidic lines, and optical fibers. The location of these components within the bending section impacts performance and stability of the bending section. All beams have an imaginary line within the body what will remain the same length when straight or bent, this line is termed the Neutral Axis of the structure. The neutral axis region does not experience any strain or stress. Typically, material that falls on either side of this line will experience strain and will either be extended or compressed. The inside of the bend will compress and the outside of the bend will extend. See FIG. 1 for an illustration of the neutral axis along with its relationship to the inner and outer bend surfaces.

Figure 2:
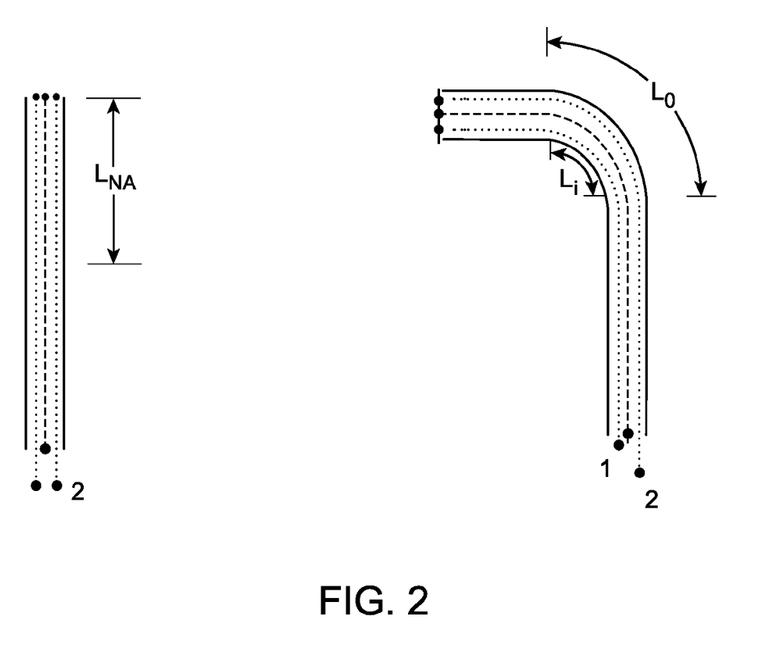
FIG. 2 is a view to facilitate description of a neutral axis.

For example, if the ancillary components are placed outside of the neutral axis region, they will slide in and out of the bending section if they are able to float relative to the bending section. Otherwise, the components will buckle or stretch due to the axial forces being imposed. FIG. 2 depicts an illustration of the relationship of components placed away from the components neutral axis.

Existing solutions for bending sections are created for small articulable instruments that is manufactured from thin walled tube. For example, intricate patterns are cut into the tubing in order to create reliefs that yield a preferential bending direction. However, if a large deflection is required; much of the tubing material will need to be removed in order to allow for such bending. Consequently, a thin walled tube with lots of its material eliminated inevitably loses much of the structure and ability to remain mechanically stable.

Therefore, it would be advantageous to have a method and apparatus for facilitating the bending of an instrument with large degrees of articulation while maintaining a sufficient amount of stiffness in order to provide stability at the end effector, all while ensuring ease of manufacturing.

SUMMARY OF THE INVENTION

Embodiments described herein are directed to a method, apparatus, and system for bending of an instrument with large degrees of articulation while maintaining ease of manufacturing.

In other embodiments, methods and apparatus for creating an articulating segment by starting with a solid rod instead of a tube. First, material is removed from the sides of the rod for enabling a bend. In one embodiment, the rod has material removed from the cross section in order to accommodate an actuation wire.

In other embodiments, the cross section accommodates ancillary components pertaining to the end effector.

One embodiment provides placing the path of the ancillary components close to the neutral axis of the bending section. Consequently, this reduces interactions between the articulation of the bending section and the ancillary components. Furthermore, resulting in a more predictable bend and end effector behavior. For example and not by way of limitation, removing material from the cross section to accommodate the articulation pull wire and the ancillary components permits manipulation of bending stiffness and the amount of opposing forces it is able to resolve during a medical procedure.

In one embodiment, the component is manufactured from a superplastic material that will be discussed later, such as, but not limited to Nitinol and other similar materials. The stiffness of the structure was manipulated via the design of the cross sectional profile in order to ensure the structure provides enough stability throughout the complete range of motion. The structure achieves a significant bend by imposing a moment on the structure and will recover to the original position when the moment is removed from the structure.

This actuation would simply require one pull wire at the tip, which would need to be pulled in order to generate a moment and relaxed to relieve the moment.

In an alternative embodiment, the component is manufactured from a superplastic material, but the cross section allows a different inner profile by incorporating the relief on the profile, the device lends itself to be manufactured using the wire EDM (Electric Discharge Machining) process without having to initially create a clearance hole.

DETAILED DESCRIPTION OF THE PREFERRED EMBODIMENT

Although certain preferred embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

The embodiments described herein are directed to an apparatus for a distal bending section of minimally invasive surgical instrument having a large degree of articulation and providing sufficient rigidity to resolve the required forces during remote surgical procedures. Other embodiments provide methods of using the distal bending section and methods for making it.

One embodiment provides placing the path of the ancillary components close to the neutral axis of the bending section. Consequently, this reduces interactions between the articulation of the bending section and the ancillary components. Furthermore, embodiments of the present invention provide a more predictable bend and end effector behavior. For example and not by way of limitation, removing material from the cross section accommodates the articulation pull wire and the ancillary components, hence, the bending stiffness can be manipulated in order to achieve a desired characteristic.

In one embodiment, the component is manufactured from a superplastic material. In one embodiment, the material is Nitinol and with superelastic phase at room and/or body temperature. Also, other embodiments include use of any super elastic alloy. In yet another embodiment, the moment of inertia was tuned such that the structure achieves a significant bend by generating a moment on the structure and recovers to the original position when the moment is removed. This actuation would simply require one pull wire at the tip, which would need to be pulled in order to generate a moment and relaxed to relieve the moment.

In an alternative embodiment, the component is manufactured from a superplastic material, but the cross section allows a different inner profile by incorporating the relief on the profile, the device lends itself to be manufactured using the wire EDM (Electric Discharge Machining) process without having to initially create a clearance hole.

Figure 3A:
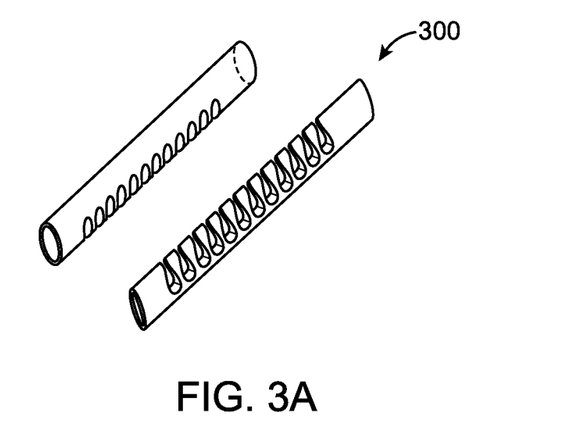
FIGS. 3A-3D depict an apparatus for a bending flexure according to a first embodiment of the present invention.
Figure 3B:
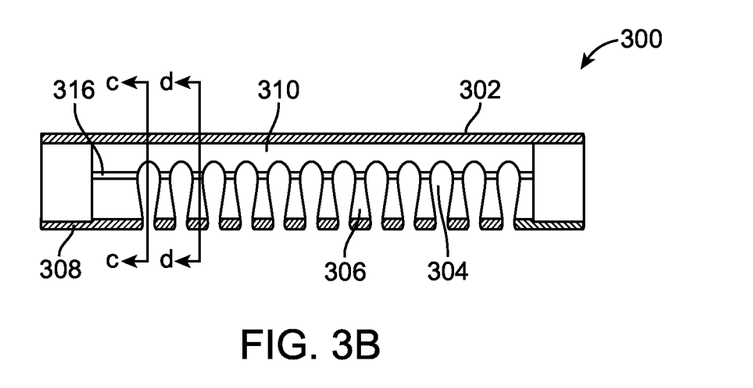

Referring to FIG. 3A, finished bending section 300 in accordance to an embodiment of the present invention is depicted. FIG. 3B is a longitudinal cross-section through the axis of bending section 300, FIG. 3C shows an axial cross-section of bending section 300 along line C of FIG. 3B, and FIG. 3D shows an axial cross-section of bending section 300 along line D of FIG. 3B.

Referring to FIG. 3B, material is removed along the top portion of a rod to create void 302, preferably along the length of the bending section. As discussed below, this void is created to assist in removal of material in the road to create the additional features of this preferred embodiment. Material is also removed from teardrop sections 304, where adjacent to teardrop section 304 material is left in place forming leaves 306. A tendon (not shown) extends through void 308 (described below) is attached at the distal end of bending section 300. When tension is applied to the tendon bending section will bend downward, as shown in the figure, and teardrop voids 304 permit leaves 306 to move inward, and a bend is realized along solid spine 310. The skilled artisan will appreciate the selection of shapes for the teardrop voids and leaves is a matter of design choice, as well as the amount of material left to form spine 310.

Figure 3C:
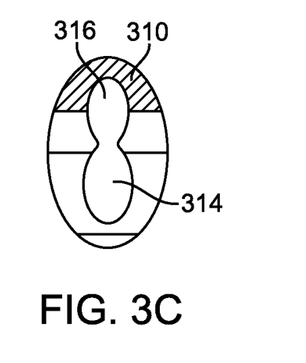
Figure 3D:
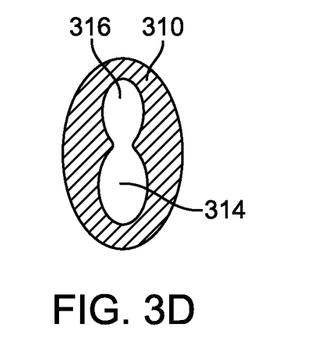

Referring now to FIG. 3C, non-cylindrical channel 312 is formed down the length of the solid rod. Preferably the outer circumference of the rod, and therefore the bending section, has an approximately cylindrical shape, similar to that of a drawn hypotube. Prior art bending sections have material cut from a hypotube, and therefore have a cylindrical inner diameter as well, which results is a uniform sidewall thickness along the length of the prior art bending section. When the outer diameter of the bending section is small, the hypotube walls do not provide sufficient strength and rigidity when large degree articulations are required and where a surgical tool at the distal end requires this rigidity to perform desired procedures. Embodiments of the present invention provide a non cylindrical channel 312 through the bending section, which permits distributing material off-axis (i.e., non-uniform wall thickness) to provide structural rigidity to the bending section, provides a pathway 314 for the tendon off-axis and a pathway 316 proximate to the neutral axis for auxiliary cables (not shown), such as tool actuating or articulating cables.

Figure 4:
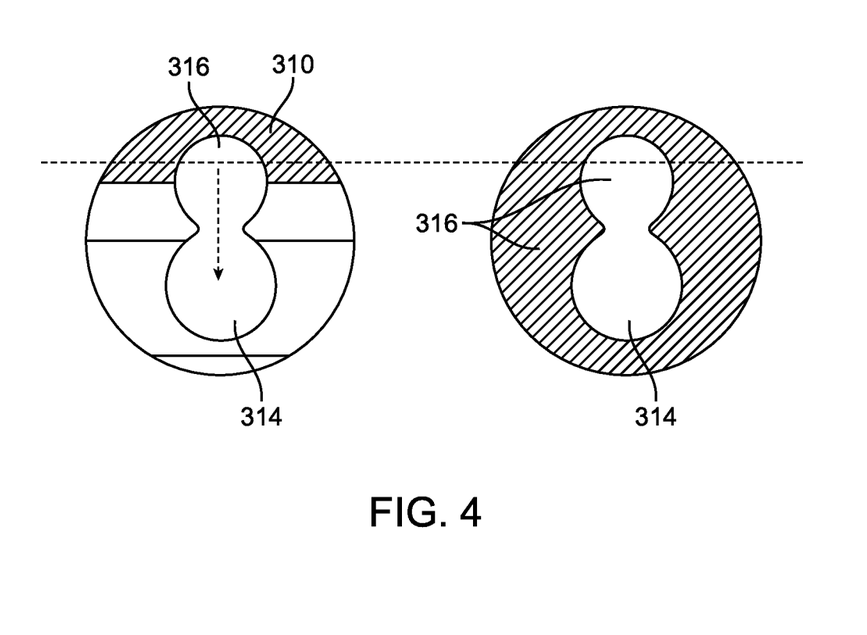
FIG. 4 is a cross section side view of FIG. 3.
Figure 5:
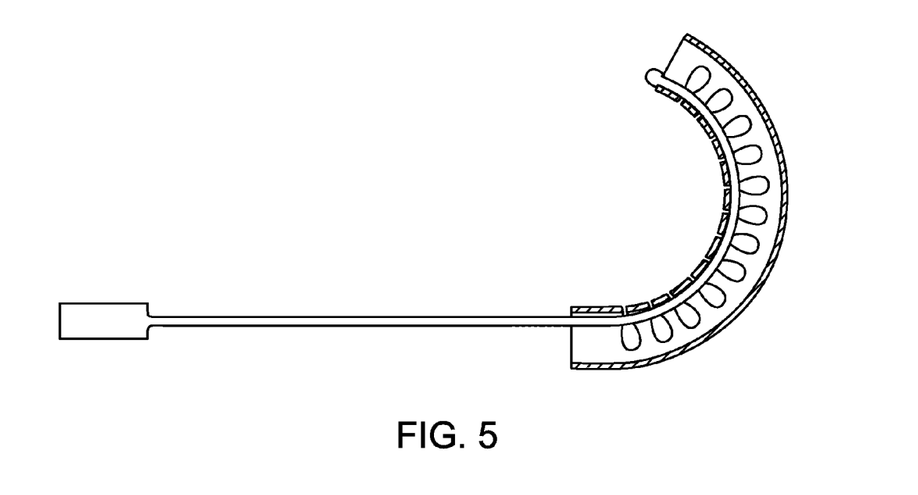
FIG. 5 is a view of a modeling representation of FIG. 3 according to a finite element analysis (FEA)

One embodiment provides for placing the path of the ancillary components as close to the neutral axis of the bending section. Consequently, this reduces interactions between the articulation of the bending section and the ancillary components. Furthermore, this embodiment provides a more predictable bend and end effector behavior. For example, removing enough material from the cross section to accommodate the articulation pull wire and the ancillary components, hence, the bending stiffness can be manipulated in order to achieve a desired characteristic. FIG. 4 is a cross section the same as shown in FIG. 3C. The location of the cross section locations relative to the structure are illustrated in FIG. 5. Section c-c demonstrates the cross section of the region 310 that will experience the bend and will contribute to the deflection of the structure. Section d-d demonstrates the region of the structure that provides a chassis 316, similar to a ribcage, to supports and house the components that are required to articulate the structure and manipulate the end effector. In this Figure, the hatched diagonal sections (referred to as hatched regions) depict a solid cross section. For example, section c-c has a solid cross section on the top portion. In contrast, section d-d has a solid cross section around the entire channel.

A dashed line near the top of the figure depicts the neutral axis of the apparatus. Also, a dashed arrow depicts the direction of the preferential bending away from the neutral axis in a downward direction.

Both section views of section c-c and d-d depict a dual oval shaped key opening, or lumen, to accommodate ancillary components (not shown) and an articulation wire (not shown). In some embodiments, the ancillary components could include any or all of the following:

Pull wires for generating actuation at the end effector;
Fibers for Illumination, laser, vision;
Pneumatics and/or hydraulics;
Electrical wires;
Open lumen for a working channel (open architecture device, end effector is passed through working channel and is interchangeable); and
A telescoping tube that supports the end effector In one embodiment, the top opening, or lumen, accommodates the ancillary components and the bottom opening accommodates the articulating wire that controls the bending of the apparatus. However, the skilled artisan appreciates different lumen configurations and placements based at least in part on the medical, surgical, or other application of the bending apparatus may be used without deviating from the present invention.

FIG. 5 is a view of a modeling representation of FIG. 3 according to a finite element analysis (FEA) which shows the interaction between the articulation wire and the flexure.

Figure 6:
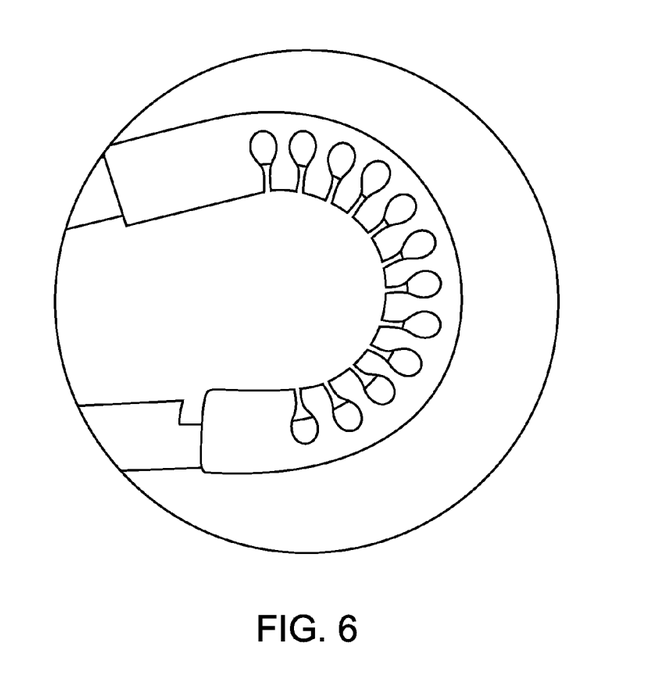
FIG. 6 is a view depicted an articulated position of the first embodiment depicted in FIG. 3.

FIG. 6 is a view depicting an articulated position of the the embodiment depicted in FIGS. 3-4. This photograph was captured under a microscope and exemplifies the uniform bending of the structure. In one embodiment, the degree of articulation is based at least in part on the amount of reliefs/voids along the length of the structure. In this embodiment, one aspect of the relief also allows the structure a hard stop (a feedback of hitting a barrier) when the leaves come in contact. Consequently, embodiments of the present invention help to prevent over articulation and potential damage to the structure.

Figure 7:
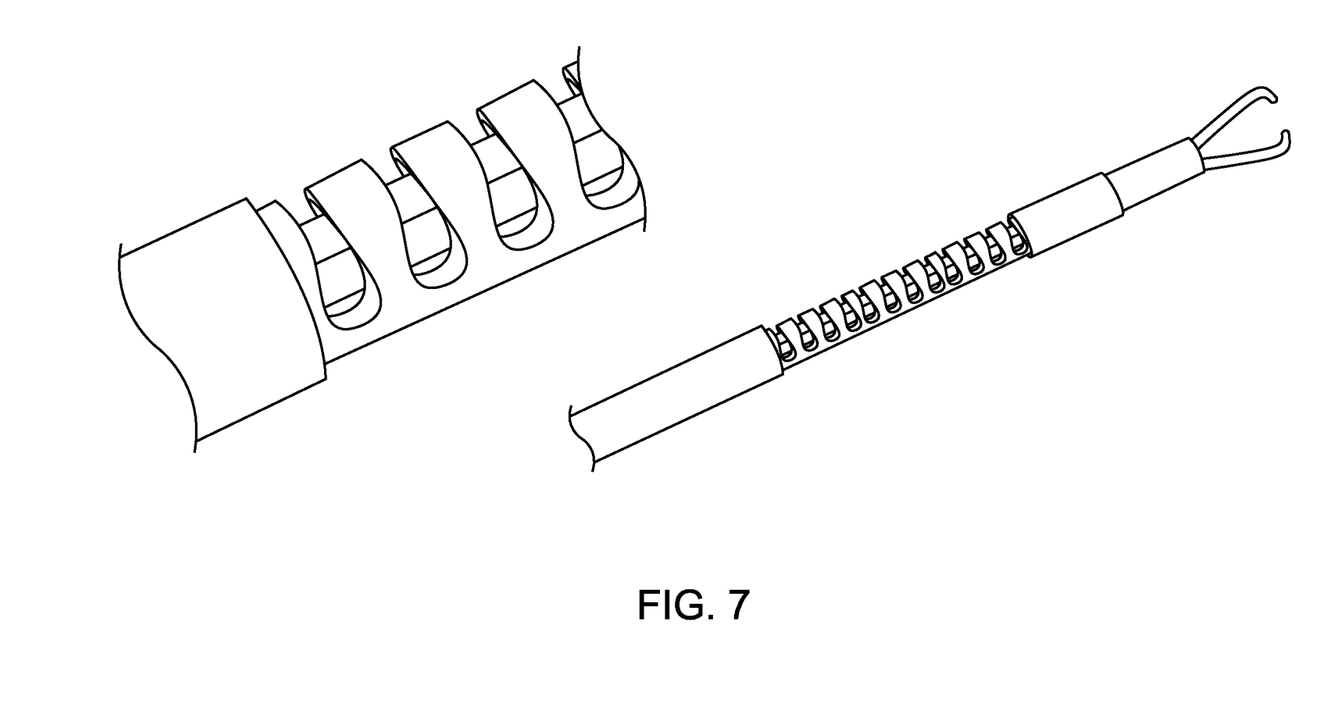
FIG. 7 is an isometric view of an assembly, wherein the flexure subject matter is incorporated into an end effector, according to one embodiment of the present invention.
Figure 8:
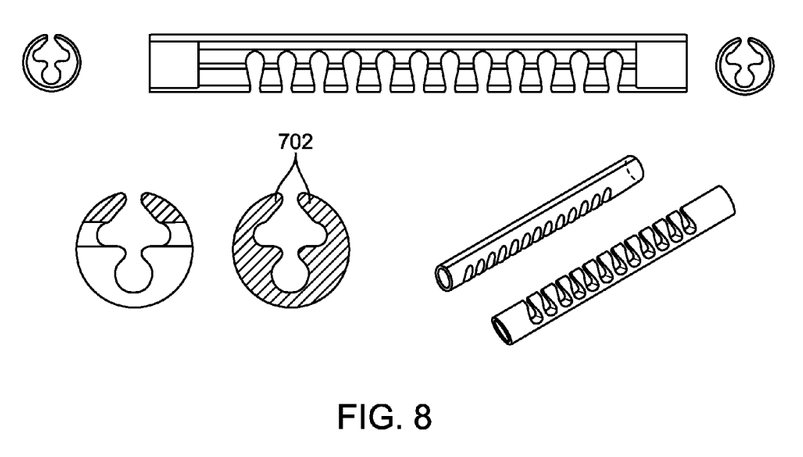
FIG. 8 depicts an apparatus for a bending flexure according to a second embodiment of the present invention.
Figure 9:
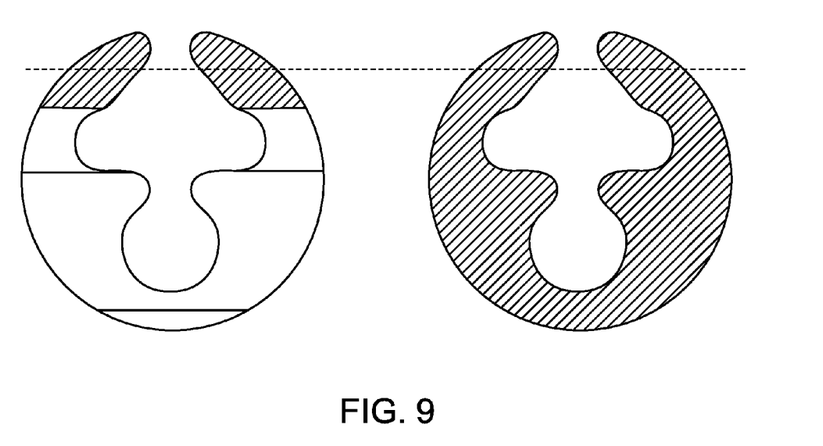
FIG. 9 is a cross section side view of FIG. 8.

FIG. 7 is an isometric view of an assembly, wherein the flexure subject matter is incorporated into an end effector, according to one embodiment of the claimed subject matter in the present invention;

FIG. 8 depicts an apparatus for a bending flexure according to another embodiment of the present invention. The skilled artisan will appreciate the shape of non-cylindrical channel 312 can be varied to achieve desired bending and rigidity properties of the bending section. The cross section of the design depicted in FIG. 8 (shown in FIG. 9), permits the inner profile to break out. By incorporating this relief on the profile, the device lends itself to be manufactured using the wire EDM process without having to initially create a clearance hole FIG. 9 is a cross section side view of FIG. 8. The two struts 702 on flexure #2 (FIG. 7) tend to bend about the neutral axis, but also slightly into the center of the cross section. This bending characteristic will result in the break out "gap" to start to close as the flexure is articulated, and will eventually close completely during large articulations.

Also, in this second embodiment, an opening allows for lateral insertion of ancillary components. The concept of having a break out on the inner profile also has a benefit during the assembly process. For example, there is an available gap through the piece, the articulation wire and ancillary components can be inserted laterally instead of axially. This assembly option also allows the flexure to replaced without having to sever the articulation wire.

Figure 10:
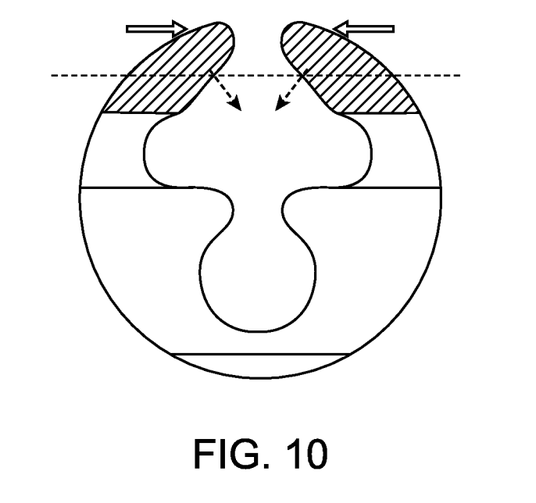
FIG. 10 is a cross section side view that depicts bending behavior of FIG. 9.

FIG. 10 is a cross section side view that depicts bending behavior of the embodiment depicted in FIG. 8-9. During operation, the gap will tend to close as the flexure is articulated and will therefore minimize the possibility of having the ancillary components "escape" the inner profile lumens. If the presence of the gap is of concern, the component can still be manufactured with a gap and then "shape set" in order to close the gap before integration into an assembly.

Elements or components shown with any embodiment herein are exemplary for the specific embodiment and may be used on or in combination with other embodiments disclosed herein. While the invention is susceptible to various modifications and alternative forms, specific examples thereof have been shown in the drawings and are herein described in detail. The invention is not limited, however, to the particular forms or methods disclosed, but to the contrary, covers all modifications, equivalents and alternatives thereof.

What is claimed is:

1. A bending section to carry a tool for use in noninvasive medical procedures, the bending section comprising:
   an actuation wire;
   a rod having an approximately cylindrical outer circumference and a neutral axis;
   a top portion along a length of the rod;
   a bottom portion along the length of the rod, wherein at least a section of the bottom portion of the cylindrical rod is formed without material;
   a non-cylindrical channel through the entire rod, the non-cylindrical channel comprising a top pathway along the top portion and proximate the neutral axis, a bottom pathway along the bottom portion and off-axis from the neutral axis, and a narrowed region therebetween connecting the top and bottom pathways, wherein the rod has a greater wall thickness at the narrowed region than at the top and bottom pathways, wherein the actuation wire is positioned within the bottom pathway to articulate the rod, wherein the actuation wire is in contact with a surface that forms the non-cylindrical channel, and wherein the top pathway is configured to accommodate at least one ancillary component to be in proximity to the neutral axis of the rod;
   a plurality of first sections alternatingly adjacent to a plurality of second sections along the length of the rod, wherein the plurality of first sections is formed without material to form a plurality of partial voids next to the plurality of second sections, such that the partial voids permit bending of the rod along the top portion of rod.

2. The bending section of claim 1 wherein the non-cylindrical channel comprises a joined dual circle or joined dual oval shaped lumen that accommodates the at least one ancillary component and the off-axis actuation wire, respectively, and wherein each of the top and bottom pathways comprise a single circle or a single oval shape.

3. The bending section of claim 1 wherein the off-axis actuation wire comprises a pull wire.

4. The bending section of claim 1 wherein the at least one ancillary component is one or more of a pull wire, an actuation wire for an end effector, an optical fiber, an electrical wire, a pneumatic component, a hydraulic component, an open lumen, or a telescoping tube.

5. The bending section of claim 1 wherein the cross section of the rod material facilitates increased stiffness support relative to that possible with a constant wall thickness.

6. The bending section of claim 1 wherein the first sections that are formed without material are teardrop shaped.

7. The bending section of claim 1 wherein the second sections that are next to the first sections are leaf shaped as defined by adjacent tear-shaped cutouts from the first sections.

8. The bending section of claim 1 wherein the rod is formed from a superplastic material.

9. The bending section of claim 8 wherein the superplastic material comprises Nitinol.

10. An apparatus to facilitate bending of an instrument comprising:
an actuation wire;
a rod with a non-cylindrical lumen;
the rod with a first and a second cross sectional shape of the rod lumen,
the first configured to facilitate a bend and to accommodate the actuation wire, the actuation wire being positioned within the rod at the first cross sectional shape, the actuation wire being in contact with a surface that forms the non-cylindrical lumen and configured to articulate the rod;
and the second to facilitate at least one ancillary component to be in proximity to a neutral axis of the rod,
wherein the first and the second cross-sectional shapes are open to one another with a narrowed region therebetween, the rod having a greater wall thickness at the narrowed region than at the top and bottom pathways, and
wherein the non-cylindrical lumen is a joined dual oval or joined dual circle shaped lumen that accommodates the ancillary component and actuation wire, wherein each of the first and second cross-sectional shapes comprise a single oval or a single circle shape.

11. The apparatus of claim 10 wherein the cross section of the rod material facilitates increased stiffness support relative to that possible with a constant wall thickness.

12. The apparatus of claim 10 wherein the rod is formed from a superplastic material.

13. The apparatus of claim 12, wherein the superplastic material comprises Nitinol.

14. An apparatus to facilitate bending of an instrument comprising:
an actuation wire;
a rod with a non-cylindrical channel and a neutral axis, the rod with a first and a second cross-section of the rod, to facilitate a bend and to accommodate the actuation wire; and
the non-cylindrical channel comprising a first pathway to facilitate at least one ancillary component to be in proximity to the neutral axis of the rod and a second pathway open to the first pathway with a narrowed region therebetween, the rod having a greater wall thickness at the narrowed region than at the top and bottom pathways, wherein the apparatus is coupled to an end effector, and
wherein the actuation wire is positioned within the second pathway to articulate the rod, the actuation wire being in contact with a surface that forms the non-cylindrical channel, and
wherein the first and second pathways form a dual oval or a dual circle shaped lumen that accommodates the ancillary component and actuation wire, the first pathway comprising a single first oval or a single first circle to accommodate the ancillary component and the second pathway comprising a single second oval or a single second circle to accommodate the actuation wire.

15. The apparatus of claim 14 wherein the second cross section facilitates increased stiffness support relative to the first cross section.

16. The apparatus of claim 14 wherein the rod is formed from a superplastic material.

17. The apparatus of claim 16, wherein the superplastic material comprises Nitinol.

18. The apparatus of claim 14 wherein the at least one ancillary component is one or more of a pull wire, an actuation wire for the end effector, an optical fiber, an electrical wire, a pneumatic component, a hydraulic component, an open lumen, or a telescoping tube.

* * * * *